United States Patent [19]

Brodeur et al.

[11] Patent Number: 5,503,992
[45] Date of Patent: Apr. 2, 1996

[54] **DNA ENCODING THE 15KD OUTER MEMBRANE PROTEIN OF *HAEMOPHILUS INFLUENZAE***

[75] Inventors: Bernard R. Brodeur; Josee Hamel, both of Ottawa, Canada; Robert S. Munson, Jr., Ballwin; Susan Grass, St. Louis, both of Mo.

[73] Assignees: Washington University, St. Louis, Mo.; Her Majesty the Queen in right of Canada, as represented by the Minister of Health and Welfare Canada, Ottawa, Canada

[21] Appl. No.: 61,314

[22] Filed: Sep. 7, 1993

[51] Int. Cl.⁶ .................... A61K 39/02; A61K 39/102; C07H 21/02; C12P 21/06
[52] U.S. Cl. .................... 435/69.3; 536/22.1; 536/23.1; 536/23.7; 530/300; 424/184.1; 424/185.1; 424/256.1; 435/6
[58] Field of Search .................... 435/69.3, 252.2, 435/252.8, 320.1; 424/184.1, 185.1, 256.1; 536/22.1, 23.1, 23.7

[56] References Cited

PUBLICATIONS

Young et al PNAS 80:1194–1198, 1983.
Dugourd et al, Abstracts of Gen. Meeting ASM p. 88, Abstract B–373.
Green et al Infection and Immunity 55: 2878–2883, 1987.
Grass et al, Abstracts of Gen Meeting of ASM p. 105, Abst. D–57.
Humel et al J. Med Microbiol 23: 163–70, 1987, Abstract Only.

*Primary Examiner*—Hazel F. Sidberry
*Attorney, Agent, or Firm*—George A. Seaby

[57] ABSTRACT

Murine monoclonal antibodies directed against a novel outer membrane protein (OMP) of *Haemophilus influenzae* have been isolated and characterized. The gene encoding of the outer membrane protein has also been isolated and characterized. Portions of the DNA sequence of the 15 kD OMP gene are useful as probes to diagnose the presence of *Haemophilus influenzae* in samples. These DNA's also make available polypeptide sequences of immunoreactive epitopes encoded within the gene, thus permitting the production of polypeptides which are useful as standards or reagents in diagnostic tests and/or as components of vaccines. Monoclonal antibodies directed against epitopes of the 15 kD OMP are also useful for diagnostic tests and as therapeutic agents for passive immunization.

5 Claims, 4 Drawing Sheets

```
         10        20        30        40        50        60
GATCCCACCTTGTTTATTCCAATAATGGAACTTTATTTTATTAAAGGTATCTAAGTAGCA 70        80        90       100       110       120
CCCTATATAGGGATTAATTAACGAGGTTTAATAATGAACTTTAACTAAAATTTTACCAGC 130       140       150       160       170       180
ATTTGCTGCTGTAGTCTGTATTATCTGCTTGTGCAAAGGATGCACCTGAAATGACAAAAT
                                                    MetThrLysS 190       200       210       220       230       240
CATCTGCGCAAATAGCTGAAATGCAAACACTTCCAACAATCACTGATAAAACAGTTGTAT
erSerAlaGlnIleAlaGluMetGlnThrLeuProThrIleThrAspLysThrValValT 250       260       270       280       290       300
ATTCCTGCAATAAACAAACGGTGACTGCTGTGTATCAATTTGAAAACCAAGAACCAGTTG
yrSerCysAsnLysGlnThrValThrAlaValTyrGlnPheGluAsnGlnGluProValA 310       320       330       340       350       360
CTGCAATGGTAAGTGTGGGCGATGGCATTATTGCCAAAGATTTTACTCGTGATAAATCAC
laAlaMetValSerValGlyAspGlyIleIleAlaLysAspPheThrArgAspLysSerG 370       380       390       400       410       420
AAAATGACTTTACAAGTTTCGTTTCTGGGGATTATGTTTGGAATGTAGATAGTGGCTTAA
lnAsnAspPheThrSerPheValSerGlyAspTyrValTrpAsnValAspSerGlyLeuT 430       440       450       460       470       480
CGTTAGATAAATTTGATTCTGTTGTGCCTGTCAATTTAATTCAAAAAGGTAAATCTAGCG
hrLeuAspLysPheAspSerValValProValAsnLeuIleGlnLysGlyLysSerSerA 490       500       510       520       530       540
ATAATATCATCGTCAAAAATTGTGATGTAAACGTAAAAGCAACTAAAAAAGCAAATTTAT
spAsnIleIleValLysAsnCysAspValAsnValLysAlaThrLysLysAlaAsnLeu*

550       560       570       580       590       600
AATTAATCCCAAATGACCAGCATAATTGCTGGTTATTTATCTTCCTCGAGGGGAGATTTT
oc
        610       620       630       640       650       660
TTCTTGA
```

FIG. 5

DNA ENCODING THE 15KD OUTER MEMBRANE PROTEIN OF *HAEMOPHILUS INFLUENZAE*

BACKGROUND OF THE INVENTION

1. Field of the Invention

This invention relates to the 15 kD outer membrane protein of *Haemophilus influenzae* type b and nontypable *Haemophilus influenzae*.

For the sake of simplicity, *Haemophilus influenzae* is hereinafter referred to as *H. influenzae*.

2. Discussion of the Prior Art

*Haemophilus influenzae* type b is a major cause of meningitis and other invasive bacterial diseases in children under the age of five. Efficacious vaccines have been produced. The vaccines contain the type b capsular polysaccharide conjugated to a carrier protein. Nontypable *H. influenzae* cause surface mucosal infections in children and adults. Such organisms also cause invasive disease in children in the developing world and immunocompromised patients. The vaccines which have been developed to prevent disease due to type b organisms are not effective against nontypable *H. influenzae*.

SUMMARY OF THE INVENTION

Outer membrane proteins elicit antibodies which are protective in animal models and therefore should be considered as components in the next generation of vaccines designed to prevent both serotype b and nontypable Haemophilus disease.

The object of the invention is to clone the gene for this *H. influenzae* protein, and to determine the DNA sequence thereof.

Accordingly, the present invention relates to a recombinant polynucleotide comprising a nucleotide sequence for the 15 kD protein of *Haemophilus influenzae* type b and nontypable *Haemophilus influenzae*, said protein having the amino acid sequence as follows:

```
          10         20         30         40         50         60
GATCCCACCTTGTTTATTCCAATAATGGAACTTTATTTTATTAAAGGTATCTAAGTAGCA 70         80         90        100        110        120
CCCTATATAGGGATTAATTAACGAGGTTTAATAATGAACTTTAACTAAAATTTTACCAGC 130        140        150        160        170        180
ATTTGCTGCTGTAGTCTGTATTATCTGCTTGTGCAAAGGATGCACCTGAAATGACAAAAT
                                                    Met Thr Lys  S 190        200        210        220        230        240
CATCTGCGCAAATAGCTGAAATGCAAACACTTCCAACAATCACTGATAAAACAGTTGTAT
er  Ser Ala Gln Ile Ala Glu Met Gln Thr Leu Pro Thr Ile Thr Asp Lys Thr Val Val T 250        260        270        280        290        300
ATTCCTGCAATAAACAAACGGTGACTGCTGTGTATCAATTTGAAAACCAAGAACCAGTTG
yr  Ser Cys Asn Lys Gln Thr Val Thr Ala Val Tyr Gln Phe Glu Asn Gln Glu Pro Val A 310        320        330        340        350        360
CTGCAATGGTAAGTGTGGGCGATGGCATTATTGCCAAAGATTTTACTCGTGATAAATCAC
la Ala Met Val Ser Val Gly Asp Gly Ile Ile Ala Lys Asp Phe Thr Arg Asp Lys Ser G 370        380        390        400        410        420
AAAATGACTTTACAAGTTTCGTTTCTGGGGATTATGTTTGGAATGTAGATAGTGGCTTAA
ln Asn Asp Phe Thr Ser Phe Val Ser Gly Asp Tyr Val Trp Asn Val Asp Ser Gly Leu T 430        440        450        460        470        480
CGTTAGATAAATTTGATTCTGTTGTGCCTGTCAATTTAATTCAAAAAGGTAAATCTAGCG
hr  Leu Asp Lys Phe Asp Ser Val Val Pro Val Asn Leu Ile Gln Lys Gly Lys Ser Ser A 490        500        510        520        530        540
ATAATATCATCGTCAAAAATTGTGATGTAAACGTAAAAGCAACTAAAAAAGCAAATTTAT
sp  Asn Ile Ile Val Lys Asn Cys Asp Val Asn Val Lys Ala Thr Lys Lys Ala Asn Leu *

550        560        570        580        590        600
AATTAATCCCAAATGACCAGCATAATTGCTGGTTATTTATCTTCCTCGAGGGGAGATTTT
oc 610        620        630        640        650        660
TTCTTGA    (SEQ ID. NOS: 1 and 2)
```

Nucleotide Sequence Coding for a Common Outer Membrane Protein from *H. influenzae* and Monoclonal Antibodies The 15 kD outer membrane protein described herein is conserved among type b and nontypable *H. influenzae*. Epitopes on the native protein are recognized by the murine monoclonal antibodies 6B11, 1A6, and 5E6. The epitopes are present on the surface of intact *H. influenzae* cells. The gene for the 15 kD protein has been cloned and the DNA sequence thereof has been determined. The gene, when expressed in an appropriate host/vector system, produces a recombinant protein which is reactive with the monoclonal antibodies. Since the protein is antigenically highly conserved, it should receive serious consideration for inclusion in a vaccine to prevent *H. influenzae* disease. Moreover monoclonal antibodies and DNA probes may be used as a diagnostic tool to detect the presence of *H. influenzae*.

DESCRIPTION OF THE PREFERRED EMBODIMENT GENERATION OF MONOCLONAL ANTIBODIES

Monoclonal antibodies (Mabs) were obtained from two independent fusion experiments. Mab 1A6 was generated from Balb/c mice immunized with sarcosyl-insoluble proteins of nontypable *H. influenzae* MTL6 as described by Hamel et al [see Journal of General Microbiology (1992), 138, 161–168] and monoclonal antibodies 6B11 and 5E6, were produced from mice immunized with outer membranes extracted from nontypable *H. influenzae* 12085 by the lithium chloride method described by Hamel et al [see J. Med. Microbiology, (1987) 23 163–170]. Isotype analysis revealed that the 1A6, 6B11 and 5E6 hybridomas secreted immunoglobulin IG2a, IG1 and IG3 respectively.

Figure 1:
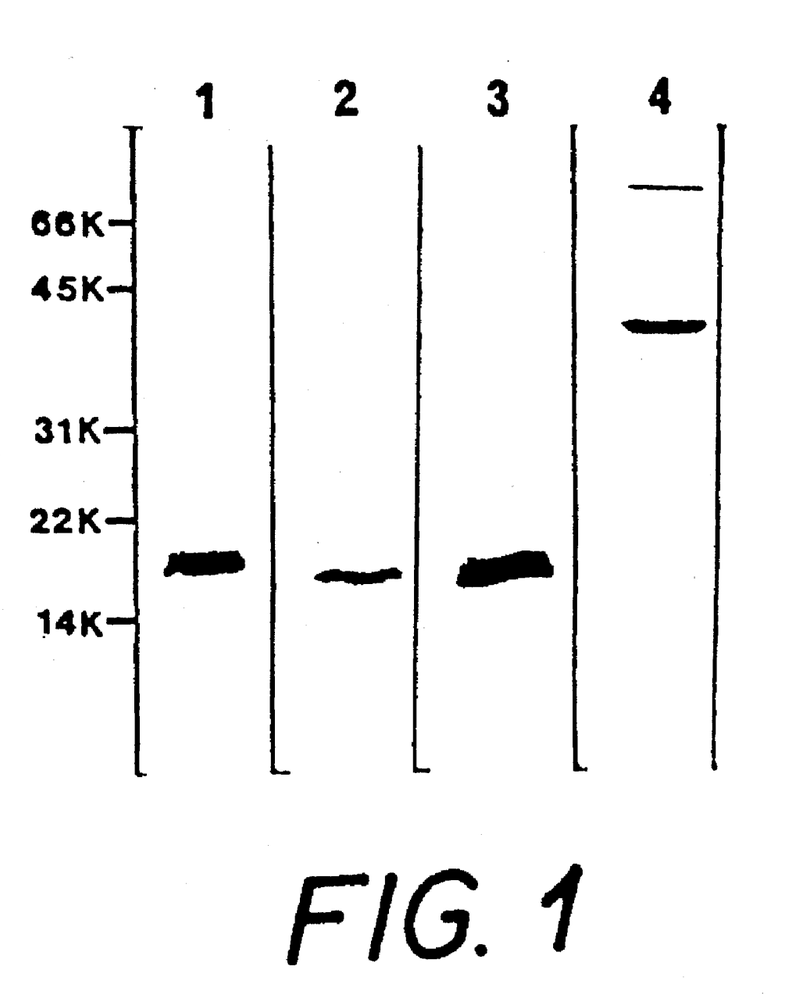
FIG. 1 is a Western blot analysis of *H. influenzae* with monoclonal antibodies.

Referring to FIG. 1, Western Immunoblotting analysis of outer membrane preparations was performed. Outer membrane preparations were fractionated on 16% SDS-PAGE, transferred to nitrocellulose, and probed with Mab 1A6 (lane 1), 6B11 (lane 2), 5E6 (lane 3) and porin-specific Mab P2-18 (lane 4). The analysis indicated that the monoclonal antibodies were directed against a protein with an apparent mass of 15 kD. Antibody accessibility radioimmunoassay [see Proulx et al, Infection and Immunity (1991)59, 963–970] indicated that monoclonal antibodies bound to surface-exposed epitopes on both type b and nontypable *H. influenzae* isolates.

CONSERVATION OF 15 KD-EPITOPES

A total of 193 *H. influenzae* isolates were tested by dot blot immunoassay for their reactivity with monoclonal antibodies 1A6, 6B11 and 5E6.

TABLE 1

Characteristics of *H. influenzae* strains tested for monoclonal antibody reactivities

| Strains | Number Reactive/ Total Number[a] |
|---|---|
| *H. influenzae* serotype b; | |
| Division 1; Clonal group A1[b] | 27/27 |
| Clonal group A2 | 59/59 |
| Clonal group B1 | 5/5 |
| Division 2; Clonal group J | 1/1 |
| *H. influenzae* serotype a; | |
| Division 1 | 2/2 |
| Division 2 | 2/2 |
| *H. influenzae* serotype d; | 2/2 |

TABLE 1-continued

Characteristics of *H. influenzae* strains tested for monoclonal antibody reactivities

| Strains | Number Reactive/ Total Number[a] |
|---|---|
| Division 1 | |
| *H. influenzae* nontypable | 95/95 |
| Other gram-negative species[c] | 0/19 |

[a]Reactivity of MAb 6B11, and 5E6 was tested individually by blot immunoassay.
[b]The chromosomal genotypes of *H. influenzae* expressing serotype a, b and d capsule were previously characterized by Dr. James Musser (see J. Musser et al "Global Genetic STructure and Molecular Epidemiology of Encopsulated *Haemophilus Influenzae*, Reviews of Infectious Diseases 12, 75–111).
[c]Nineteen isolates representing 19 other gram-negative species were tested. These are listed in Table 2.

TABLE 2

Non-*H. influenzae* isolates tested

Alcaligenes odorans
Citrobacter freundii
Flavobacterium odoratum
Edwardsiella tarda
Enterobacter cloaca
Enterobacter aerogenes
Klebsiella pneumoniae
Moraxella catharrhalis
Neisseria lactamica
Neisseria perflava
Neisseria subflava
Pseudomonas aeruginaosa
Proteus vulgaris
Providencia rettgeri
Serratia marcescens
Salmonella thyphimurium
Shigella flexneri
Shigella sonnei
Xanthomonas maltophilia

MOLECULAR CLONING OF THE GENE FOR THE 15 KD OUTER MEMBRANE PROTEIN

Figure 2:
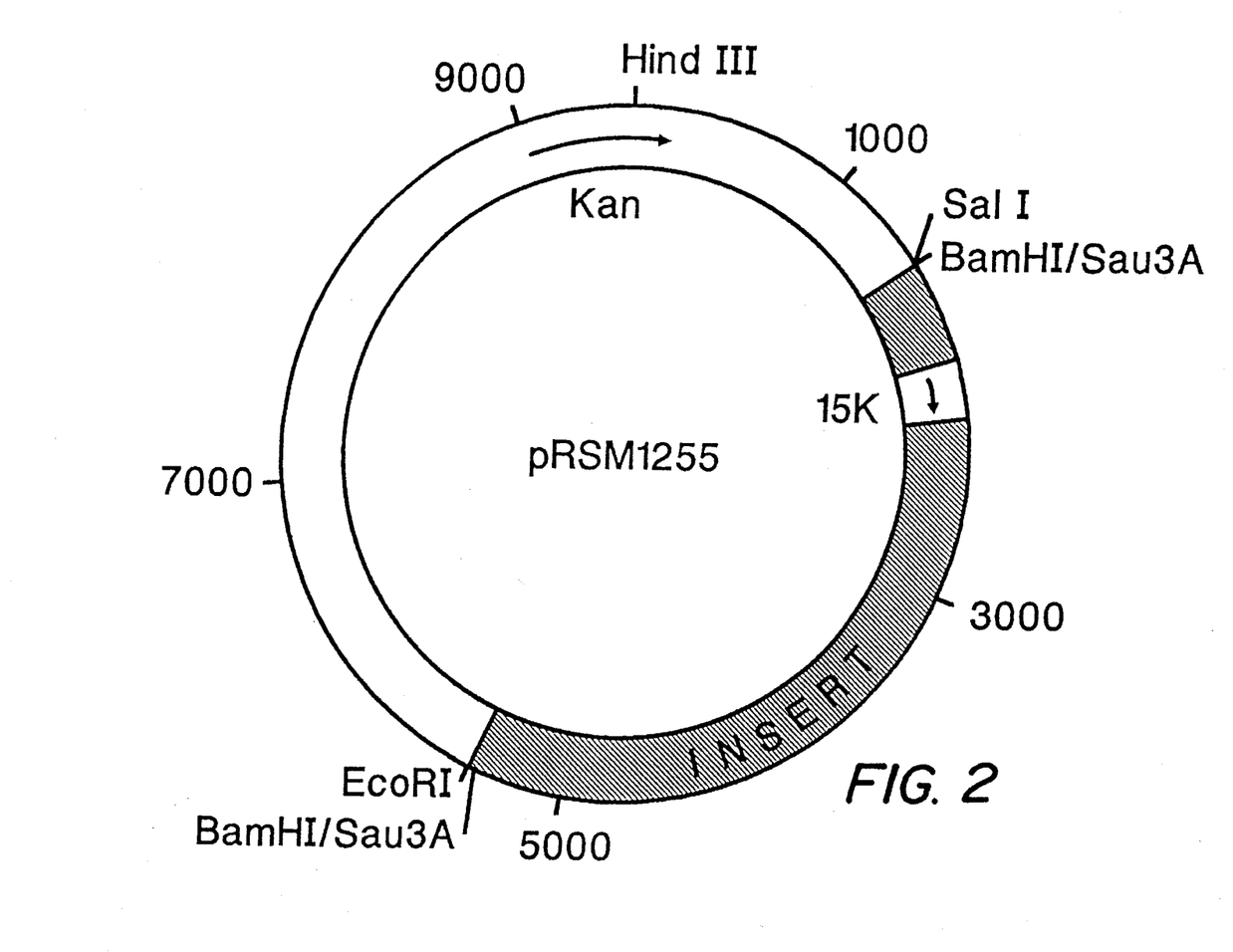
FIG. 2 is a partial restriction map of plasmid pRSM1255 which contains the gene for the 15 kD outer membrane protein from *H. influenzae* type b strain 1613.
Figure 3:
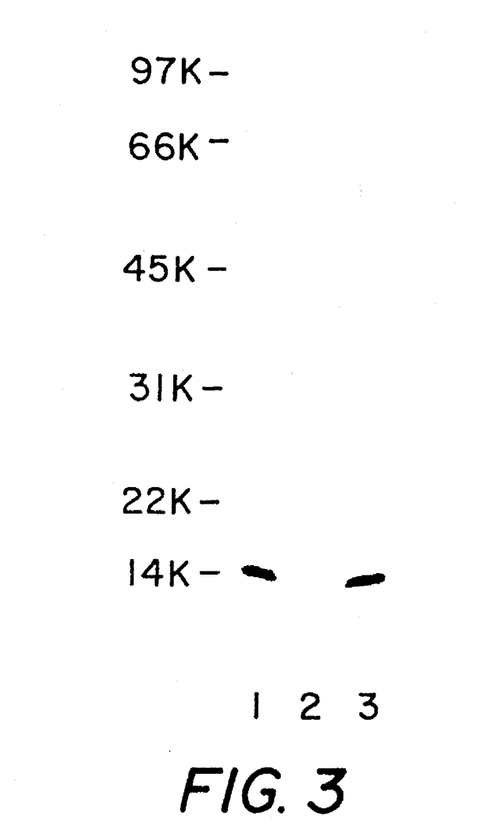
FIG. 3 is a Western blot analysis of the expression of the recombinant 15 kD protein.

A lambda EMBL3 genomic library of DNA from *H. influenzae* strain 1613 was immunologically screened with murine monoclonal antibody 6B11 as described by Munson and Grass [see Infection and Immunity (1988) 561 2235–2242]. An immunologically reactive clone was isolated by plaque purification. A liquid lysate was prepared and DNA was purified from a Promega lambda DNA kit according to the manufacturer's directions. The Haemophilus insert was identified as a SalI fragment of approximately 16 kb. DNA from the lambda clone was partially digested with Sau3A and fragments of approximately 3–6 kb were isolated by preparative agarose gel electrophoresis. The 3–6 kb fragments were ligated into the low copy number vector pGD103 [see Deich et al, Journal of Bacteriology (1988) 489– 498] which had been digested sequentially with BamHI and alkaline phosphatase. The ligation mixture was transformed into *E. coli* strain LE392 and the cells were plated on LB agar containing 35 µg/ml of kanamycin. Immunologically reactive colonies were identified by screening with murine Mab 6B11. Strain LE392/pRSM1255 was saved for further study. As shown in FIG. 2 plasmid pRSM1255 has an insert of approximately 3.8 kb. Strain LE392/pRSM1255 produces the full size protein as determined by Western blot (see FIG. 3). Membrane preparations were fractionated by SDS-PAGE, transferred to nitrocellulose and probed with murine monoclonal antibody 6B11. Lane 1 is the total membrane preparation of *H. influenzae* strain 1613; lane 2 is the total membrane preparation of *E. coli* strain LE392/pGD103 and lane 3 is the total membrane preparation of *E. coli* strain LE392/pRSM1255. The full size 15 Kd protein is produced by *E. coli* strain LE392/pRSM1255.

Figure 4:
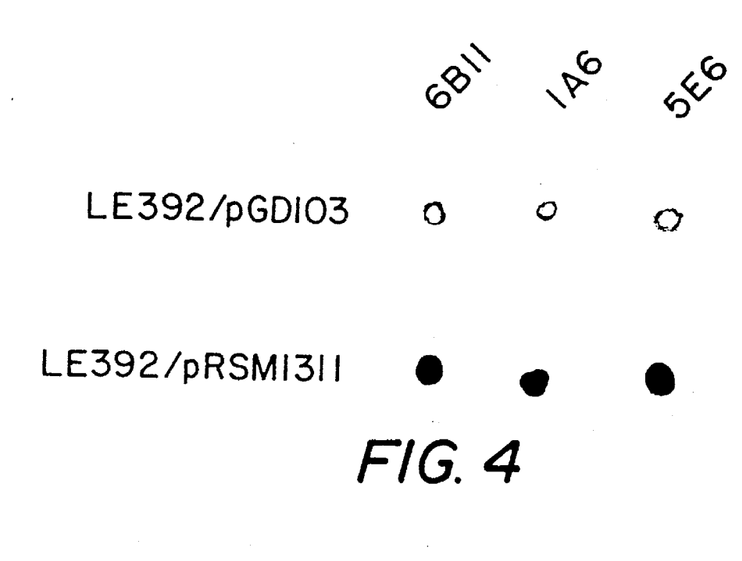
FIG. 4 is a dot blot immunoassay of extracts of *E. coli* strains LE392/pGD103 and LE392/pRSM1311.
Figure 5:
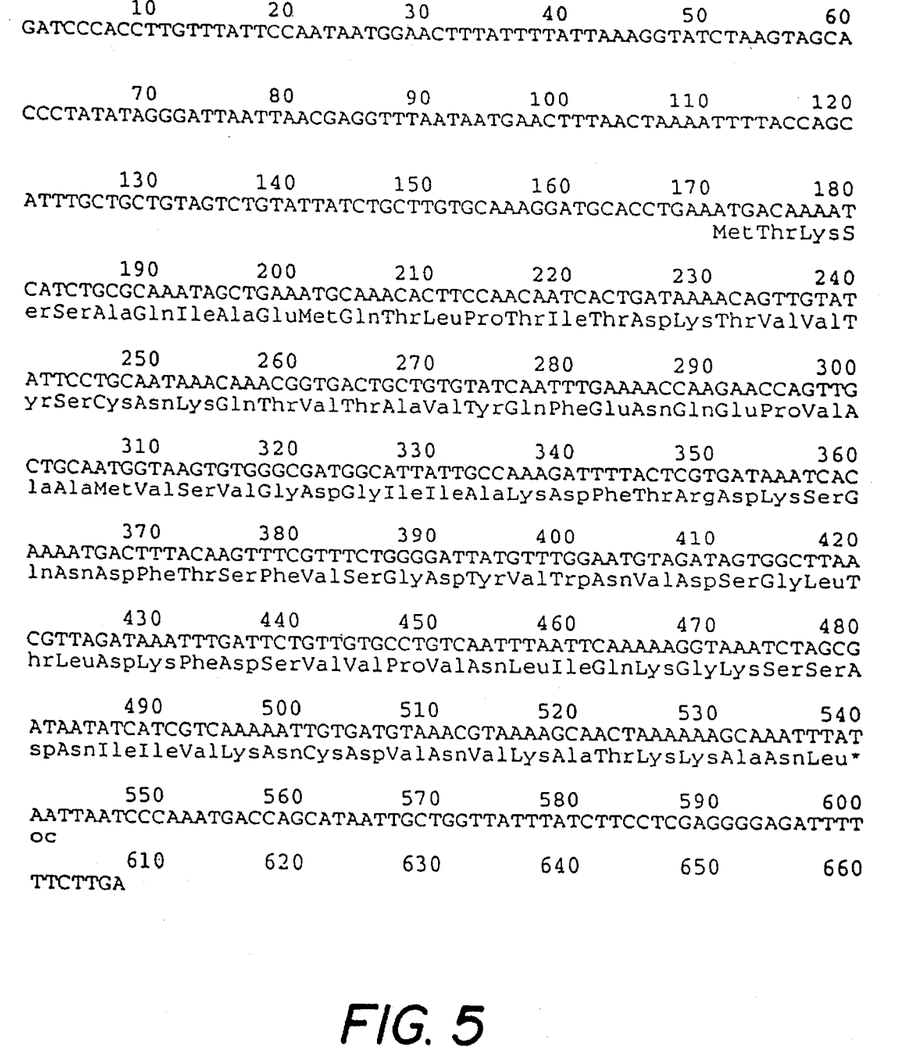
FIG. 5 is the amino acid sequence for the polynucleotide of the present invention.

In order to further subclone the gene for sequencing, pRSM1255 was partially digested with Sau3A, fragments of approximately 0.5 to 1.5 kb were isolated, ligated into BamHI-treated pGD103 and transformed into *E. coli* strain LE392. An immunologically positive clone, designated LE392/pRSM1311 was saved for further analysis. Western blot analysis employing Mab 6B11 indicated that the full size protein was produced by this strain (data not shown). The Haemophilus insert in pRSM1311 is approximately 0.6 kb in size. Extracts of *E. coli* strain LE392/pRSM1311 react with all three murine Mabs (FIG. 4). 5 µg of cell extracts were applied to the nitrocellulose and probed with Mabs 3B11, 1A6, and 5E6.

SEQUENCE ANALYSIS

The insert was cloned into M13mp18 and M13mp19 as a SalI to EcoRI fragment and sequenced in both directions. A 369 codon open reading frame was identified encoding a protein composed of 123 amino acids and having a molecular weight of 13,460. The open reading frame is notable for a lysine at position 3 and a cysteine at position 26 suggesting that the protein is a lipoprotein with a 25 amino acid leader peptide.

DNA and protein sequence analysis were done using Gen Bank (a trademark of NIH) and EMBL (from European Molecular Biology Organization) data bases. The nucleotide and derived amino acid sequence of the 15 kD outer membrane protein of *H. influenzae* type b, strain 1613 is set out in Table 3.

TABLE 3

MW for gene product = 13460.    Number of amino acids = 123

```
         10        20        30        40        50        60
GATCCCACCTTGTTTATTCCAATAATGGAACTTTATTTTATTAAAGGTATCTAAGTAGCA 70        80        90       100       110       120
CCCTATATAGGGATTAATTAACGAGGTTTAATAATGAACTTTAACTAAAATTTTACCAGC 130       140       150       160       170       180
ATTTGCTGCTGTAGTCTGTATTATCTGCTTGTGCAAAGGATGCACCTGAAATGACAAAAT
                                                  Met Thr Lys S 190       200       210       220       230       240
CATCTGCGCAAATAGCTGAAATGCAAACACTTCCAACAATCACTGATAAAACAGTTGTAT
er  Ser Ala Gln Ile Ala Glu Met Gln Thr Leu Pro Thr Ile Thr Asp Lys Thr Val Val T 250       260       270       280       290       300
ATTCCTGCAATAAACAAACGGTGACTGCTGTGTATCAATTTGAAAACCAAGAACCAGTTG
yr  Ser Cys Asn Lys Gln Thr Val Thr Ala Val Tyr Gln Phe Glu Asn Gln Glu Pro Val A 310       320       330       340       350       360
CTGCAATGGTAAGTGTGGGCGATGGCATTATTGCCAAAGATTTTACTCGTGATAAATCAC
la  Ala Met Val Ser Val Gly Asp Gly Ile Ile Ala Lys Asp Phe Thr Arg Asp Lys Ser G 370       380       390       400       410       420
AAAATGACTTTACAAGTTTCGTTTCTGGGGATTATGTTTGGAATGTAGATAGTGGCTTAA
ln  Asn Asp Phe Thr Ser Phe Val Ser Gly Asp Tyr Val Trp Asn Val Asp Ser Gly Leu T 430       440       450       460       470       480
CGTTAGATAAATTTGATTCTGTTGTGCCTGTCAATTTAATTCAAAAAGGTAAATCTAGCG
hr  Leu Asp Lys Phe Asp Ser Val Val Pro Val Asn Leu Ile Gln Lys Gly Lys Ser Ser A 490       500       510       520       530       540
ATAATATCATCGTCAAAAATTGTGATGTAAACGTAAAAGCAACTAAAAAAGCAAATTTAT
sp  Asn Ile Ile Val Lys Asn Cys Asp Val Asn Val Lys Ala Thr Lys Lys Ala Asn Leu *

550       560       570       580       590       600
AATTAATCCCAAATGACCAGCATAATTGCTGGTTATTTATCTTCCTCGAGGGGAGATTTT
oc 610       620       630       640       650       660
TTCTTGA
```

The sequence was found to have no significant homology to any known proteins including two previously described Haemophilus outer membrane lipoproteins of similar size.

The research described herein was supported in part by United States Public Health Service grant R01AI17572 from the National Institutes of Health.

The sequence for the polynucleotide claimed in this application is as follows:

| SEQUENCE DESCRIPTION: SEQ ID NO: 1: | |
|---|---:|
| GATCCCACCT TGTTTATTCC AATAATGGAA CTTTATTTTA TTAAAGGTAT CTAAGTAGCA | 60 |
| CCCTATATAG GGATTAATTA ACGAGGTTTA ATAATGAACT TTAACTAAAA TTTTACCAGC | 120 |
| ATTTGCTGCT GTAGTCTGTA TTATCTGCTT GTGCAAAGGA TGCACCTGAA ATGACAAAAT | 180 |
| CATCTGCGCA AATAGCTGAA ATGCAAACAC TTCCAACAAT CACTGATAAA ACAGTTGTAT | 240 |
| ATTCCTGCAA TAAACAAACG GTGACTGCTG TGTATCAATT GAAAACCAA GAACCAGTTG | 300 |
| CTGCAATGGT AAGTGTGGGC GATGGCATTA TTGCCAAAGA TTTTACTCGT GATAAATCAC | 360 |
| AAAATGACTT TACAAGTTTC GTTTCTGGGG ATTATGTTTG GAATGTAGAT AGTGGCTTAA | 420 |
| CGTTAGATAA ATTTGATTCT GTTGTGCCTG TCAATTTAAT TCAAAAAGGT AAATCTAGCG | 480 |
| ATAATATCAT CGTCAAAAAT TGTGATGTAA ACGTAAAAGC AACTAAAAAA GCAAATTTAT | 540 |
| AATTAATCCC AAATGACCAG CATAATTGCT GGTTATTTAT CTTCCTCGAG GGGAGATTTT | 600 |
| TTCTTGA | 607 |

The amino acid sequence for the outer membrane protein of haemophilus influenzae claimed in this application is as follows:

| SEQUENCE DESCRIPTION: SEQ ID NO: 2: |
|---|

| Met 1 | Thr | Lys | Ser | Ser 5 | Ala | Gln | Ile | Ala | Glu 10 | Met | Gln | Thr | Leu | Pro 15 | Thr |
| Ile | Thr | Asp | Lys 20 | Thr | Val | Val | Tyr | Ser 25 | Cys | Asn | Lys | Gln | Thr 30 | Val | Thr |
| Ala | Val | Tyr 35 | Gln | Phe | Glu | Asn | Gln 40 | Glu | Pro | Val | Ala | Ala 45 | Met | Val | Ser |
| Val | Gly 50 | Asp | Gly | Ile | Ile | Ala 55 | Lys | Asp | Phe | Thr | Arg 60 | Asp | Lys | Ser | Gln |
| Asn 65 | Asp | Phe | Thr | Ser | Phe 70 | Val | Ser | Gly | Asp | Tyr 75 | Val | Trp | Asn | Val | Asp 80 |
| Ser | Gly | Leu | Thr | Leu 85 | Asp | Lys | Phe | Asp | Ser 90 | Val | Val | Pro | Val | Asn 95 | Leu |
| Ile | Gln | Lys | Gly 100 | Lys | Ser | Ser | Asp | Asn 105 | Ile | Ile | Val | Lys | Asn 110 | Cys | Asp |
| Val | Asn | Val 115 | Lys | Ala | Thr | Lys | Lys 120 | Ala | Asn | Leu. | | | | | |

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
( A ) LENGTH: 607 base pairs
( B ) TYPE: nucleic acid
( C ) STRANDEDNESS: single
( D ) TOPOLOGY: linear ( i i ) MOLECULE TYPE: DNA (genomic)

( i i i ) HYPOTHETICAL: NO ( i v ) ANTI-SENSE: NO ( i x ) FEATURE:
( A ) NAME/KEY: misc_feature
( B ) LOCATION: 171..539
( D ) OTHER INFORMATION: /note="Nucleotides 171 through 539
encode the outer membrane protein of Haemophilus
Influenzae of Sequence ID No. 2."

( x i ) SEQUENCE DESCRIPTION: SEQ ID NO:1:

```
GATCCCACCT  TGTTTATTCC  AATAATGGAA  CTTTATTTTA  TTAAAGGTAT  CTAAGTAGCA    60
CCCTATATAG  GGATTAATTA  ACGAGGTTTA  ATAATGAACT  TTAACTAAAA  TTTTACCAGC   120
ATTTGCTGCT  GTAGTCTGTA  TTATCTGCTT  GTGCAAAGGA  TGCACCTGAA  ATGACAAAAT   180
CATCTGCGCA  AATAGCTGAA  ATGCAAACAC  TTCCAACAAT  CACTGATAAA  ACAGTTGTAT   240
ATTCCTGCAA  TAAACAAACG  GTGACTGCTG  TGTATCAATT  TGAAAACCAA  GAACCAGTTG   300
CTGCAATGGT  AAGTGTGGGC  GATGGCATTA  TTGCCAAAGA  TTTTACTCGT  GATAAATCAC   360
AAAATGACTT  TACAAGTTTC  GTTTCTGGGG  ATTATGTTTG  GAATGTAGAT  AGTGGCTTAA   420
CGTTAGATAA  ATTTGATTCT  GTTGTGCCTG  TCAATTTAAT  TCAAAAAGGT  AAATCTAGCG   480
ATAATATCAT  CGTCAAAAAT  TGTGATGTAA  ACGTAAAAGC  AACTAAAAAA  GCAAATTTAT   540
AATTAATCCC  AAATGACCAG  CATAATTGCT  GGTTATTTAT  CTTCCTCGAG  GGGAGATTTT   600
TTCTTGA                                                                  607
```

( 2 ) INFORMATION FOR SEQ ID NO:2:

( i ) SEQUENCE CHARACTERISTICS:
( A ) LENGTH: 123 amino acids
( B ) TYPE: amino acid
( D ) TOPOLOGY: linear ( i i ) MOLECULE TYPE: peptide ( i i i ) HYPOTHETICAL: NO ( i x ) FEATURE:
( A ) NAME/KEY: misc_feature
( B ) LOCATION: 1..123
( D ) OTHER INFORMATION: /note="Nucleotides 171 through 539
encode the outer membrane protein of Haemophilus
Influenzae of Sequence ID No. 2."

( x i ) SEQUENCE DESCRIPTION: SEQ ID NO:2:

```
Met  Thr  Lys  Ser  Ser  Ala  Gln  Ile  Ala  Glu  Met  Gln  Thr  Leu  Pro  Thr
 1              5                        10                        15

Ile  Thr  Asp  Lys  Thr  Val  Val  Tyr  Ser  Cys  Asn  Lys  Gln  Thr  Val  Thr
                20                        25                        30
```

|       |     |     |     |     |     |     |     |     |     |     |     |     |     |     |
|-------|-----|-----|-----|-----|-----|-----|-----|-----|-----|-----|-----|-----|-----|-----|
| Ala   | Val | Tyr<br>35 | Gln | Phe | Glu | Asn | Gln<br>40 | Glu | Pro | Val | Ala | Ala<br>45 | Met | Val | Ser |
| Val   | Gly<br>50 | Asp | Gly | Ile | Ile | Ala<br>55 | Lys | Asp | Phe | Thr | Arg<br>60 | Asp | Lys | Ser | Gln |
| Asn<br>65 | Asp | Phe | Thr | Ser | Phe<br>70 | Val | Ser | Gly | Asp | Tyr<br>75 | Val | Trp | Asn | Val | Asp<br>80 |
| Ser | Gly | Leu | Thr | Leu<br>85 | Asp | Lys | Phe | Asp | Ser<br>90 | Val | Val | Pro | Val | Asn<br>95 | Leu |
| Ile | Gln | Lys | Gly<br>100 | Lys | Ser | Ser | Asp | Asn<br>105 | Ile | Ile | Val | Lys | Asn<br>110 | Cys | Asp |
| Val | Asn | Val<br>115 | Lys | Ala | Thr | Lys | Lys<br>120 | Ala | Asn | Leu |

We claim:

1. The recombinant polynucleotide having the sequence

```
          10         20         30
GATCCCACCTTGTTTATTCCAATAATGGAA 40         50         60
          CTTTATTTTATTAAAGGTATCTAAGTAGCA 70         80         90
CCCTATATAGGGATTAATTAACGAGGTTTA 100        110        120
          ATAATGAACTTTAACTAAAATTTTACCAGC 130        140        150
ATTTGCTGCTGTAGTCTGTATTATCTGCTT 160        170        180
          GTGCAAAGGATGCACCTGAaATGACAAAAT
                                 Met Thr Lys S 190        200        210
CATCTGCGCAAATAGCTGAAATGCAAACAC
er Ser Ala Gln Ile Ala Glu Met Gln Thr L 220        230        240
          TTCCAACAATCACTGATAAAACAGTTGTAT
          eu Pro Thr Ile Thr Asp Lys Thr Val Val T 250        260        270
ATTCCTGCAATAAACAAACGGTGACTGCTG
yr Ser Cys Asn Lys Gln Thr Val Thr Ala V 280        290        300
          TGTATCAATTTGAAAACCAAGAACCAGTTG
          al Tyr Gln Phe Glu Asn Gln Glu Pro Val A 310        320        330
CTGCAATGGTAAGTGTGGGCGATGGCATTA
la Ala Met Val Ser Val Gly Asp Gly Ile I 340        350        360
          TTGCCAAAGATTTTACTCGTGATAAATCAC
          le Ala Lys Asp Phe Thr Arg Asp Lys Ser G 370        380        390
AAAATGACTTTACAAGTTTCGTTTCTGGGG
ln Asn Asp Phe Thr Ser Phe Val Ser Gly A 400        410        420
          ATTATGTTTGGAATGTAGATAGTGGCTTAA
          sp Tyr Val Trp Asn Val Asp Ser Gly Leu T 430        440        450
CGTTAGATAAATTTGATTCTGTTGTGCCTG
hr Leu Asp Lys Phe Asp Ser Val Val Pro V 460        470        480
          TCAATTTAATTCAAAAAGGTAAATCTAGCG
          al Asn Leu Ile Gln Lys Gly Lys Ser Ser A 490        500        510
ATAATATCATCGTCAAAAATTGTGATGTAA
sp Asn Ile Ile Val Lys Asn Cys Asp Val A 520        530        540
          ACGTAAAAGCAACTAAAAAAGCAAATTATT
          sn Val Lys Ala Thr Lys Lys Ala Asn Leu *

550        560        570
AATTAATCCCAAATGACCAGCATAATTGCT
oc 580        590        600
          GGTTATTTATCTTCCTCGAGGGGAGATTTT 610        620        630        640        650        660
TTCTTGA (SEQ. ID. NO:1)
``` encoding a polypeptide comprising immunoreactive epitopes of the 15 kD outer membrane protein of *Haemophilus influenzae*.

2. A vector comprising a recombinant polynucleotide, wherein the recombinant polynucleotide is the recombinant polynucleotide of claim 1.

3. A host cell transformed with the vector of claim 2.

4. A recombinant expression system comprising a polynucleotide encoding a polypeptide comprising one or more immunoreactive epitopes of the 15 kD outer membrane protein of claim 1, wherein the polynucleotide is operably linked to a control sequence compatible with a desired host.

5. A cell transformed with a recombinant expression system, wherein the expression system is the recombinant expression system of claim 4.

* * * * *